United States Patent
Chin

[19]

[11] Patent Number: 5,816,257

[45] Date of Patent: *Oct. 6, 1998

[54] GASLESS RETROPERITONEAL SURGICAL PROCEDURE

[75] Inventor: Albert K. Chin, Palo Alto, Calif.

[73] Assignee: Origin Medsystems, Inc., Menlo Park, Calif

[ * ] Notice: This patent issued on a continued prosecution application filed under 37 CFR 1.53(d), and is subject to the twenty year patent term provisions of 35 U.S.C. 154(a)(2). .

[21] Appl. No.: 580,083

[22] Filed: Dec. 20, 1995

[51] Int. Cl.$^6$ ..................................................... A61B 19/00
[52] U.S. Cl. ............................................. 128/898; 604/49
[58] Field of Search ..................... 606/192, 61; 600/201, 600/204, 207; 604/908, 49, 22; 623/17; 128/898

[56] References Cited

U.S. PATENT DOCUMENTS

| | | | |
|---|---|---|---|
| 4,545,374 | 10/1985 | Jacobson | 606/61 |
| 4,913,134 | 4/1990 | Luque | 606/61 |
| 5,015,255 | 5/1991 | Kuslich | 623/17 |
| 5,112,332 | 5/1992 | Cozad et al. | 606/61 |
| 5,127,912 | 7/1992 | Ray et al. | 606/61 |
| 5,195,541 | 3/1993 | Obenchain | 128/898 |
| 5,201,729 | 4/1993 | Hertzmann et al. | 128/898 |
| 5,295,994 | 3/1994 | Bonutti | 606/192 |
| 5,309,896 | 5/1994 | Moll et al. | 600/207 |
| 5,313,962 | 5/1994 | Obenchain | 128/898 |
| 5,318,586 | 6/1994 | Ereren | 606/192 |
| 5,354,266 | 10/1994 | Snoke | 128/898 |
| 5,359,995 | 11/1994 | Sewell, Jr. | 600/204 |
| 5,361,752 | 11/1994 | Moll et al. | 600/207 |
| 5,402,772 | 4/1995 | Moll et al . | 600/207 |
| 5,425,357 | 6/1995 | Moll et al. | 600/207 |
| 5,450,843 | 9/1995 | Moll et al. | 600/207 |
| 5,454,367 | 10/1995 | Moll et al. | 600/207 |
| 5,465,711 | 11/1995 | Moll et al. | 600/207 |
| 5,468,248 | 11/1995 | Chin et al. | 600/207 |
| 5,571,172 | 11/1996 | Chin | 623/1 |

*Primary Examiner*—Mickey Yu
*Assistant Examiner*—Kelly O'Hara
*Attorney, Agent, or Firm*—Fenwick & West LLP

[57] ABSTRACT

A surgical procedure includes forming an incision in a patient placed in the right lateral recumbent position to facilitate forming a retroperitoneal cavity. Dissection is formed with a balloon cannula, and the retroperitoneal cavity thus formed is then maintained by a mechanical lift or retractor positioned to elevate the wall of the cavity adjacent the patient's left side. The dissected peritoneum and the underlying bowel are displaced away from the spine by gravity with the patient thus positioned. An endoscope may be introduced into the retroperitoneal cavity to visualize surgery within the cavity including dissection of the iliopsoas muscle to facilitate discectomy and spinal fusion of adjacent vertebrae.

6 Claims, 7 Drawing Sheets

GASLESS RETROPERITONEAL SURGICAL PROCEDURE

RELATED APPLICATIONS

The subject matter of this application is related to the subject matter of pending U.S. Pat. application Sec. No. 08/290,361, entitled "Method and Apparatus for Endoscopic Grafting," filed on Aug. 15, 1994 by Albert K. Chin, now U.S. Pat. No. 5,571,172 which application is assigned to the same assignee as this application and is incorporated herein in its entirety by this reference.

FIELD OF THE INVENTION

This invention relates to method and apparatus for retroperitoneal procedures for spinal discectomy and fusion, and more particularly to method and apparatus for attaining such spinal access without insufflation to create a working cavity adjacent the spine.

BACKGROUND OF THE INVENTION

Retroperitoneal surgical procedures for creating a surgical working cavity in the region of target tissue such as the aorta are disclosed in the co-pending application cited above. Such surgical procedure uses a dissection balloon cannula in the retroperitoneum to dissect a cavity in the tissue adjacent the aorta, and to maintain the cavity using either gas insufflation or mechanical traction to support the cavity while securing a graft to the aorta.

Similar retroperitoneal procedures may be used to access the anterior portion of the spine more conveniently and less traumatically than by way of a large abdominal incision. Such a transabdominal procedure commonly involves retracting the bowel, incising the peritoneum on the back wall of the abdominal cavity, and accessing the anterior spine.

Alternatively, a retroperitoneal approach may involve an incision in the abdomen at the border of the rectus muscle, dissecting down to identify the peritoneum, dissecting the peritoneum away from the abdominal wall in a lateral then posterior direction until the spine is reached.

An endoscopic approach may be used to access the spine by either the transabdominal or the retroperitoneal procedure, as described in the literature (see, for example, U.S. Pat. Nos. 5,195,541 describing a transabdominal laparoscopic procedure, and 5,313,962 describing a retroperitoneal endoscopic procedure). These known procedures require gas insufflation to maintain the abdominal or retroperitoneal cavity, thus making it difficult to apply various instruments, for example, required for removing connective tissue or bone or disc material. Specialized instruments with round cross sectional shafts are required to facilitate sealing within valved trocar ports associated with gas insufflation. Thus conventional orthopedic instruments used in spinal surgery, including rongeurs, box cutters, scalpels, and electrocautery pencils, may not be used in insufflated endoscopic retroperitoneal cavities since the irregular cross sections of these instruments cannot be sealed against trocar valves that generally have round openings.

SUMMARY OF THE INVENTION

Accordingly, the method and apparatus of the present invention employs mechanical retraction to maintain the dissected retroperitoneal cavity and facilitate gasless retroperitoneal discectomy and fusion.

DESCRIPTION OF THE PREFERRED EMBODIMENT

Figure 1A:
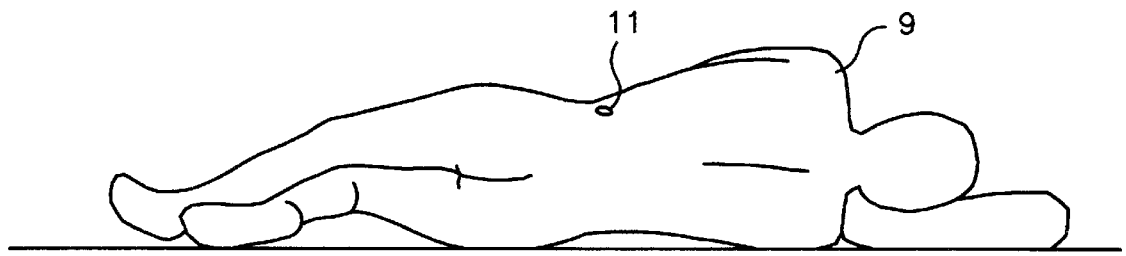
FIG. 1A is a pictorial illustration of a patient in operating position exposing the surgical site.

In accordance with the illustrated embodiment of the invention, the patient 9 is placed in a right lateral recumbent position as shown in FIG. 1A, for the advantage that gravity provides in causing the dissected peritoneal tissue and the underlying bowel to fall away from the spine. In contrast, retraction of the peritoneum and the underlying bowel is more difficult with the patient in a supine position since the spine lies under the mass of bowel.

Figure 3:
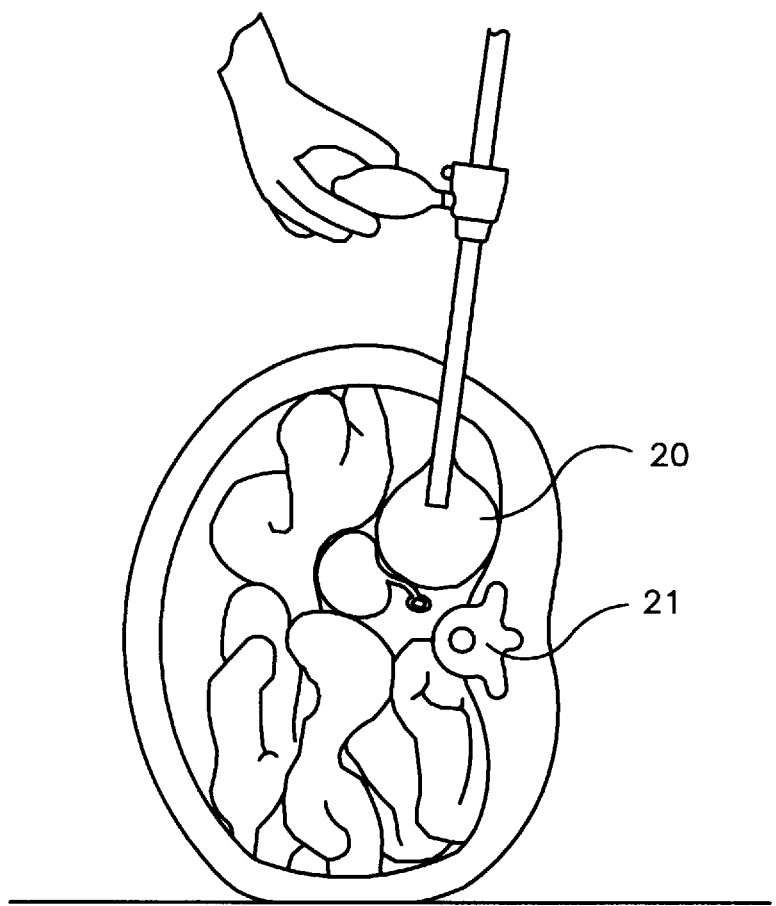
FIG. 3 is a partial sectional view showing a balloon dissection cannula inserted into the peri-renal space and inflated to form a retroperitoneal cavity.

A small skin incision 11, of approximately 2 cm in length, is made in the left flank, and manual blunt dissection of the peritoneum 13 away from the abdominal wall 15 is performed using Kelley Clamps, finger dissection, or a blunt probe 17, as shown in FIG. 1A, to the lower border of the left kidney to form a retroperitoneal cavity 19. A dissection balloon 20 is then inserted into the cavity and inflated to form a longitudinally-expanded cavity substantially aligned with the spine 21, as shown in FIG. 3, and a mechanical lift or retractor 23 (such as Laparolift, or Laparofan or Airlift forms of retractors, commercially available from Origin Med Systems, Inc.) is positioned within the cavity to support the ceiling of the cavity, as shown in FIG. 4.

Figure 4:
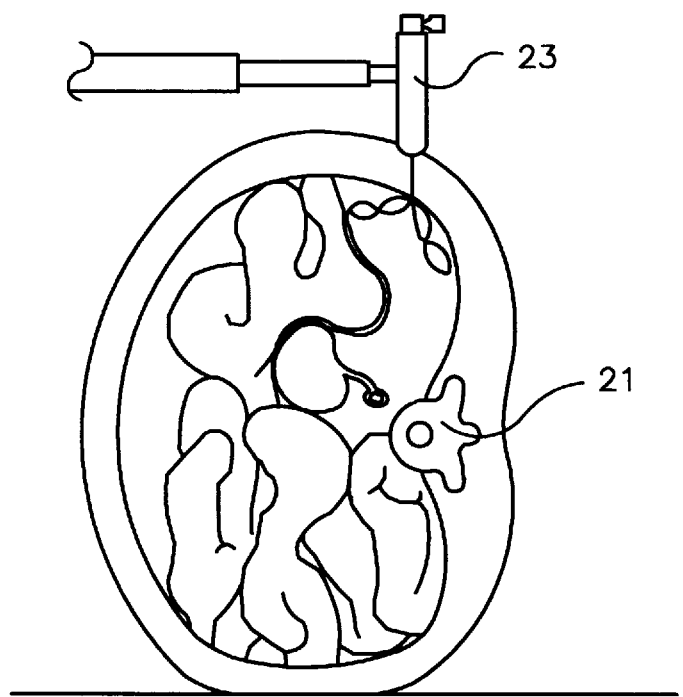
FIG. 4 is a partial sectional view showing the dissection balloon removed and a mechanical retractor inserted to lift the ceiling of the retroperitoneal cavity.

A second retractor, which may be an inflatable type, is positioned in the cavity to retract the dissected peritoneum and the bowel behind the peritoneum, as shown in FIG. 4.

Figure 5:
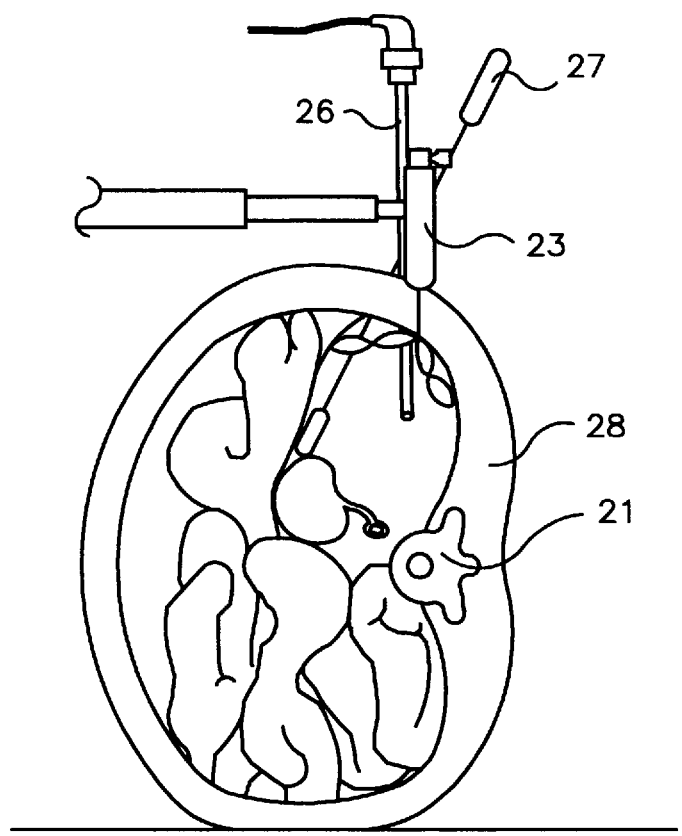
FIG. 5 is a partial sectional view showing an endoscope inserted into the cavity for visualizing the cavity, and showing other surgical instruments including a peritoneal retractor to retract the peritoneum and intra-abdominal contents and expose the iliopsoas muscle overlying the spine.

As illustrated in FIG. 5, an endoscope 26, and other surgical instruments 27, may be introduced into the cavity through the initial incision into the retroperitoneal cavity to perform the discectomy and fusion. Specifically, the discectomy procedure involves dissection of the iliopsoas muscle 28 overlying the anterior aspect of the spine 21 in order to isolate a selected disc region along the spine. The disc is removed, using rongeurs and other dissection instruments in conventional manner, and the adjacent vertebrae are fused at the level of the discectomy using bone graft and/or fixation hardware, or an implant to substitute for the removed disc, according to conventional surgical procedures.

Figure 1B:
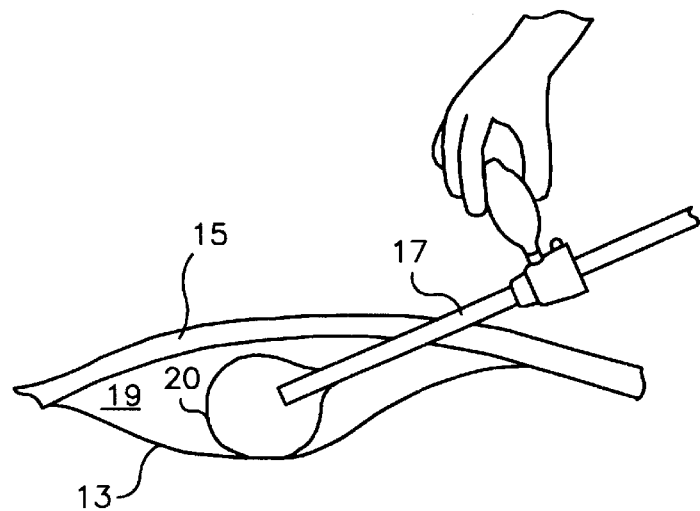
FIG. 1B is a partial sectional view showing the peritoneum bluntly dissected away from the abdominal wall.
Figure 2:
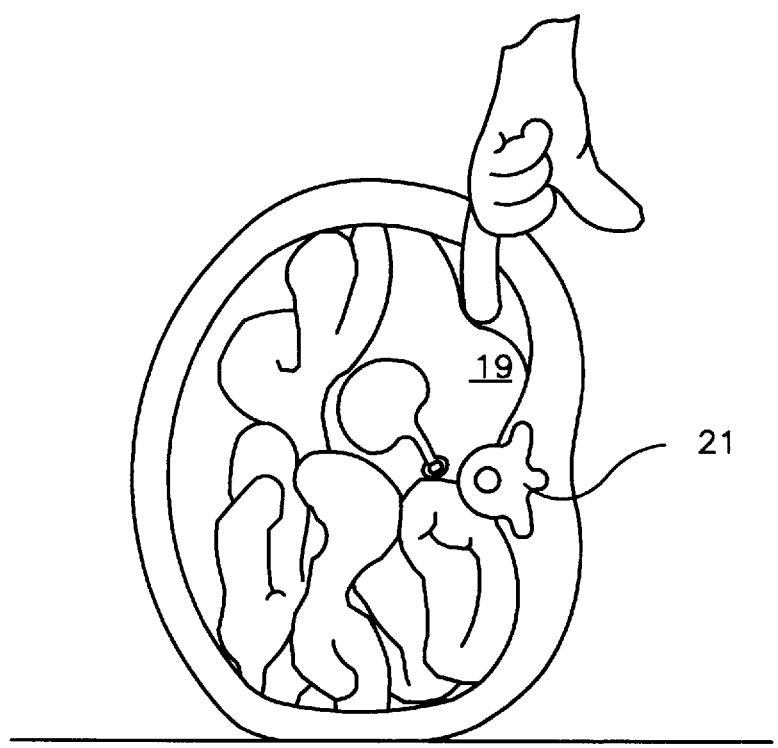
FIG. 2 is a partial sectional view showing blunt dissection of subcutaneous connective tissue to reach the peri-renal space.

In an alternative embodiment of the surgical procedures according to the present invention, the patient 9 is placed in the right lateral recumbent position, or a partial right lateral recumbent position, as shown in FIG. 1. An initial incision is made in the flank of the patient, about midway between the costal margin and the iliac crest, in the anterior auxiliary line. The overlying connective tissue and adjacent muscle tissue are bluntly dissected to reach the peri-renal space, as shown in FIG. 2. A balloon dissection cannula 20 is then inserted into the peri-renal space, and the balloon is inflated to form a retroperitoneal cavity, as shown in FIG. 3. The dissection balloon 20 is removed and a mechanical lift or retractor 23 is inserted, as shown in FIG. 4, to lift the ceiling of the retroperitoneal cavity. Referring to FIG. 5, an endoscope 26 is then inserted through the initial incision into the retroperitoneal cavity thus formed and maintained for visualizing the cavity as additional incisions are made into the cavity for placement of a peritoneal retractor and other surgical instruments selectively within the cavity. The iliopsoas muscle 28 overlying the spine 21 is dissected to expose a selected disc region along the spine 21, and the disc may be removed and the adjacent vertebrae may be fused according to conventional procedures, as described above.

Thereafter, the surgical instruments are removed from the cavity, the mechanical retractor or lift is removed from the incision to allow the peritoneum to fall back into position to eliminate the retroperitoneal cavity, and the incision is sutured.

Figure 6:
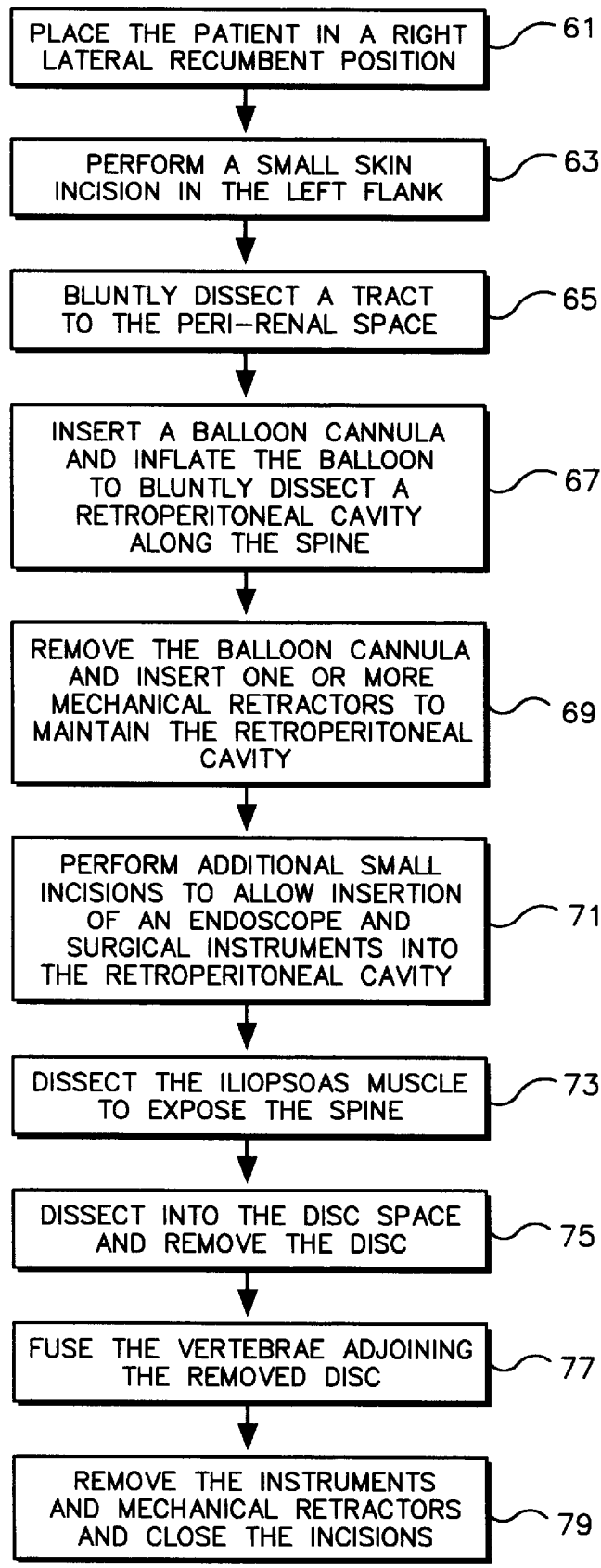
FIGS. 6 and 7 are flow charts illustrating procedures according to the present invention.

Referring now to FIG. 6, there is shown a flow chart illustrating the operating procedure involved according to one embodiment of the present invention. Specifically, the patient is place 61 in a right lateral recumbent position to derive the gravitational advantage, as previously described. A small incision is then made 63 in the left flank, and a tract is bluntly dissected 65, e.g., via finger dissection as shown in FIG. 2, to the peri-renal space. A balloon cannula is then inserted 67 into the tract thus formed, and the balloon is inflated to bluntly dissect a retroperitoneal cavity along the spine. The balloon cannula is then removed from the cavity thus formed and one or more mechanical retractors are inserted 69, e.g., to lift the cavity wall, in order to maintain the retroperitoneal cavity.

Additional small incisions into the cavity may be formed to facilitate insertion of an endoscope and other surgical instruments into the cavity. The iliopsoas muscle that overlays the spine may be dissected 73 to expose a selected intravertebral region in which dissection down to the disc space may be accomplished. The disc may then be removed 75, and the adjacent vertebrae may then be fused 77 or fixed with fixation hardware in conventional manner. Thereafter, the operative instruments and mechanical retractors may be removed 79 to facilitate restoration of the peritoneum and closure of the incision in conventional manner.

Figure 7:
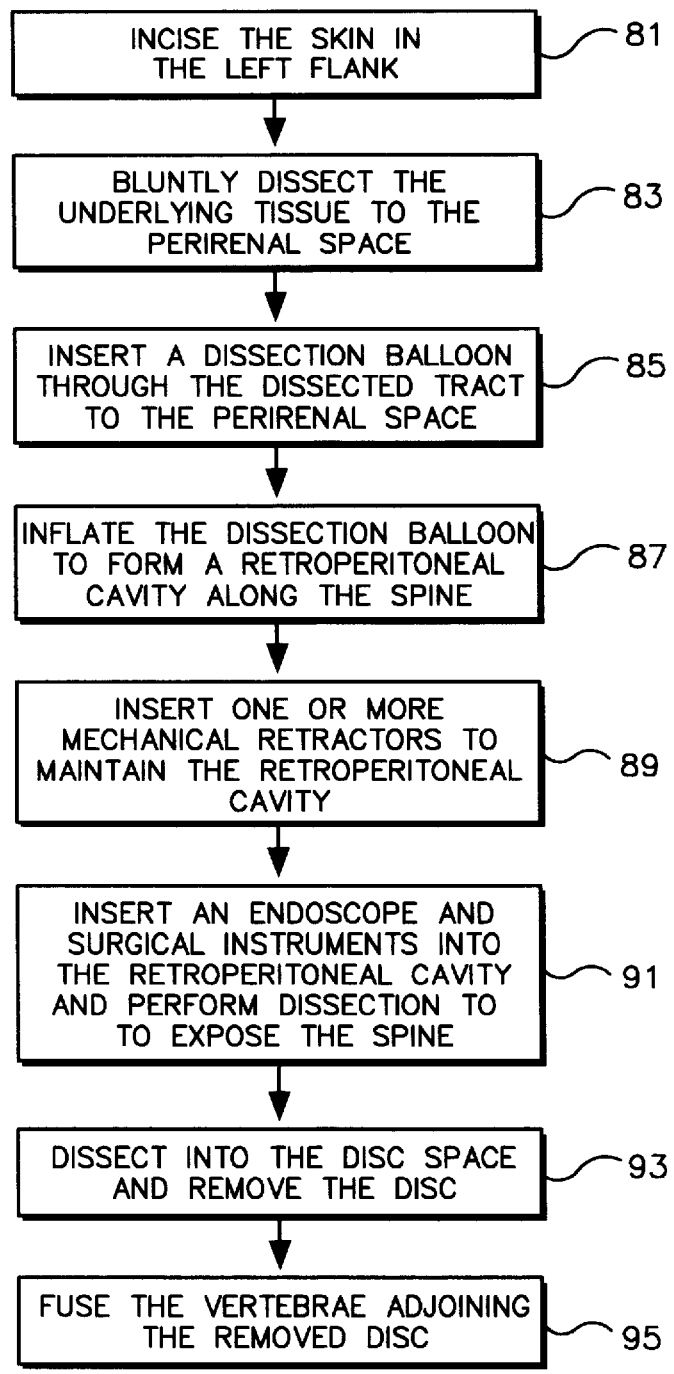

Referring now to the flow chart of FIG. 7, there is illustrated a variation of the procedure described above with reference to FIG. 6. Specifically, with the patient in the position 61 described above, an incision 81 is formed in the skin of the left flank, and the underlying tissue is bluntly dissected 83, as discussed above, to the peri-renal space. Then, a dissection balloon is inserted 85 in the bluntly dissected region and inflated 87 to form a retroperitoneal cavity along the spine. The cavity is maintained 89 mechanically, for example, using a conventional fan-type mechanical lift or retractor to elevate the top of the cavity adjacent the initial incision. An endoscope and surgical instruments are introduced 91 into the retroperitoneal cavity thus formed and maintained, through the initial or additional incisions into the cavity for dissecting tissue to expose the spine and for dissecting into the disc space 93 to remove the disc. The adjacent vertebrae may then be fused, for example, with fixation hardware or bone implant and other conventional techniques 95, and the instruments and retractors may thereafter be removed from the cavity, the peritoneum restored, and the initial and additional incisions, if any, may then be sutured in conventional manner.

Therefore, the surgical procedure according to the present invention establishes a retroperitoneal cavity for anteriorly accessing the iliopsoas muscle and the spine to facilitate discectomies and fusions without insufflation of the cavity or restrictions on surgical Instruments manipulatable within the cavity through gas-tight trocar valve ports.

I claim:

1. A method for accessing a retroperitoneal cavity in a surgical procedure on a patient comprising the steps of:

forming a small flank incision in the patient;

dissecting a cavity in the retroperitoneal region of the patient;

mechanically retracting a wall of the retroperitoneal cavity formed adjacent to the incision for maintaining the cavity without pressurized gas therein;

inserting an endoscope into the cavity for visualizing in the cavity; and inserting surgical instruments into the cavity for surgery on tissue exposed within the retroperitoneal cavity thus formed and maintained and visualized through the endoscope.

2. The method according to claim 1 in which the surgery performed within the retroperitoneal cavity includes dissection of the iliopsoas muscle down to a selected spinal disc of the patient, and a discectomy.

3. The method according to claim 1 in which the patient is placed in right lateral recumbent position to facilitate dissecting peritoneal tissue and underlying bowel of the patient displacing away from the spine under gravity.

4. The method according to claim 2 in which the surgery performed within the retroperitoneal cavity includes spinal fusion of adjacent vertebrae of the patient following discectomy.

5. The method according to claim 3 in which mechanical retraction of a cavity wall includes a fan retractor positioned, to elevate the wall of the retroperitoneal cavity adjacent the left side of the patient.

6. A method for accessing a retroperitoneal cavity in a surgical procedure on a patient comprising the steps of:

forming a small flank incision in the patient;

dissecting a cavity in the retroperitoneal region of the patient;

mechanically retracting a wall of the retroperitoneal cavity formed adjacent to the incision for maintaining the cavity open through the incision to ambient pressure;

inserting an endoscope into the cavity for visualizing in the cavity; and inserting surgical instruments into the cavity for surgery on tissue exposed with the retroperitoneal cavity thus formed and maintained and visualized through the endoscope.

* * * * *